United States Patent
Thompson et al.

(10) Patent No.: US 9,790,138 B2
(45) Date of Patent: Oct. 17, 2017

(54) CONVERSION OF POLYESTER-CONTAINING FEEDSTOCKS INTO HYDROCARBON PRODUCTS

(71) Applicant: BIOSYNTHETIC TECHNOLOGIES, LLC., Irvine, CA (US)

(72) Inventors: Travis Thompson, Anaheim, CA (US); Jeremy Forest, Honolulu, HI (US)

(73) Assignee: Boisynthetic Technologies, LLC, Irvine, CA (US)

( * ) Notice: Subject to any disclaimer, the term of this patent is extended or adjusted under 35 U.S.C. 154(b) by 46 days.

(21) Appl. No.: 14/831,723

(22) Filed: Aug. 20, 2015

(65) Prior Publication Data

US 2016/0060186 A1    Mar. 3, 2016

Related U.S. Application Data

(60) Provisional application No. 62/044,401, filed on Sep. 1, 2014.

(51) Int. Cl.

| | |
|---|---|
| *C07C 5/22* | (2006.01) |
| *C07C 1/207* | (2006.01) |
| *C07C 5/02* | (2006.01) |
| *C07C 4/02* | (2006.01) |
| *C10L 1/04* | (2006.01) |
| *C10G 3/00* | (2006.01) |
| *C10G 65/04* | (2006.01) |

(52) U.S. Cl.
CPC .............. *C07C 1/2078* (2013.01); *C07C 4/02* (2013.01); *C07C 5/02* (2013.01); *C07C 5/22* (2013.01); *C10G 3/40* (2013.01); *C10G 3/42* (2013.01); *C10G 3/50* (2013.01); *C10G 65/04* (2013.01); *C10L 1/04* (2013.01); *C07C 2521/06* (2013.01); *C07C 2521/18* (2013.01); *C07C 2523/755* (2013.01); *C07C 2523/78* (2013.01); *C07C 2523/883* (2013.01); *C07C 2529/14* (2013.01); *Y02P 30/20* (2015.11)

(58) Field of Classification Search
CPC .................................................. C07C 1/2078

USPC ......................................... 585/254, 310, 733
See application file for complete search history.

(56) References Cited

U.S. PATENT DOCUMENTS

| | | | |
|---|---|---|---|
| 4,992,605 A | 2/1991 | Craig et al. | |
| 7,928,273 B2 | 4/2011 | Bradin | |
| 7,968,757 B2 | 6/2011 | Abhari et al. | |
| 8,084,655 B2 | 12/2011 | Dindi et al. | |
| 2009/0000984 A1 | 1/2009 | De Graaf et al. | |
| 2009/0018235 A1* | 1/2009 | Nascimento | C08L 67/04 523/128 |
| 2009/0124713 A1* | 5/2009 | Ayasse | B01J 23/8896 518/715 |
| 2010/0228067 A1* | 9/2010 | Peterson | C10G 1/002 585/500 |
| 2012/0022305 A1 | 1/2012 | Yao et al. | |
| 2012/0053375 A1* | 3/2012 | Tagawa | C10M 101/02 585/1 |
| 2012/0172609 A1* | 7/2012 | Bredsguard | C07C 69/675 554/122 |
| 2012/0222991 A1 | 9/2012 | O'Connor et al. | |

FOREIGN PATENT DOCUMENTS

WO    2014092896    6/2014

OTHER PUBLICATIONS

Modak, S.N.; Kane, J.G. "Studies in Estolides. I. Kinetics of Estolide Formation and Decomposition", Journal of the American Oil Chemists' Society, 42 (1965), pp. 428-432.*

* cited by examiner

*Primary Examiner* — In Suk Bullock
*Assistant Examiner* — Aaron Pierpont
(74) *Attorney, Agent, or Firm* — Jeremy Forest

(57) ABSTRACT

Provided herein are methods of processing polyester-containing feedstocks to provide hydrocarbon products. Exemplary feedstocks include those containing estolide compounds, which may be processed under thermal and/or catalytic conditions to provide at least one hydrocarbon product.

20 Claims, No Drawings

US 9,790,138 B2

CONVERSION OF POLYESTER-CONTAINING FEEDSTOCKS INTO HYDROCARBON PRODUCTS

FIELD

The present disclosure relates to the processing of polyester compounds and compositions to provide one or more hydrocarbon products. In certain embodiments, the process comprises the deoxygenation of polyester compounds such as estolides.

BACKGROUND

Natural and synthetic esters such as polyesters and estolides have been described as a viable source of biodegradable base stocks to formulate lubricants. Such base stocks may be used in the production of lubricating oils for automobiles, industrial lubricants, and lubricating greases. Finished lubricants typically comprise the base oil and additives to help achieve desired viscometric properties, low temperature behavior, oxidative stability, corrosion protection, demulsibility and water rejection, friction coefficients, lubricities, wear protection, air release, color and other properties. Though such bio-based formulations provide an environmentally-friendly alternative to petroleum-based lubricants, such products must be handled appropriately once the useful life of the product is completed. Accordingly, there remains a need for methods of processing, recycling, and/or reusing these bio-based products.

SUMMARY

Described herein are polyester compounds and compositions, including products containing estolide base oils, and methods of processing, recycling, and/or reusing the same. In certain embodiments, such compositions may include new or used lubricant products containing one or more estolide-type compounds.

In certain embodiments, the compositions are processed through a method that includes providing a feedstock comprising at least one polyester compound, and converting the at least one polyester compound into at least one hydrocarbon product. In certain embodiments, the at least one polyester compound comprises an estolide. In certain embodiments, converting the at least one polyester compound comprises deoxygenation. In certain embodiments, converting the at least one polyester compound comprises decarbonylation and/or decarboxylation. In certain embodiments, converting the at least one polyester compound comprises exposing said polyester to heating conditions. In certain embodiments, the process comprises contacting the at least one polyester compound with at least one catalyst, optionally in the presence of elevated heat and/or pressure. In certain embodiments, the at least one hydrocarbon product undergoes further processing to provide at least one second hydrocarbon product.

DETAILED DESCRIPTION

The market for used motor oil has stymied many recycling and reclamation efforts. In some cases, the market for used motor oil has largely been geared to limited processing steps which convert the used motor oil into a low quality fuel such as bunker oil (#6 fuel oil). In other instances, a limited amount of used motor oil is reclaimed and converted into a recycled motor oil product. Because used motor oil retains a high energy potential, it may be processed in a manner that allows access to this energy.

In certain embodiments is provided a method of processing a composition comprising polyester-containing product, wherein at least one polyester compound is converted into at least one hydrocarbon product. In certain embodiments, the at least one polyester comprises an estolide compound. In certain embodiments, the at least one hydrocarbon product can undergo further processing to provide at least one second hydrocarbon product. In certain embodiments, the at least one hydrocarbon product and/or at least one second hydrocarbon product can provide a useful source of fuel. Exemplary fuels include, but are not limited to, gasoline, jet fuel, and diesel fuel.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)NH$_2$ is attached through the carbon atom.

"Alkoxy" by itself or as part of another substituent refers to a radical —OR$^{31}$ where R$^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

"Estolide" as used herein may generally refer to a certain oligomeric/polymeric compounds comprising at least one carboxylic group bound to the hydrocarbon backbone (i.e., alkyl residue) of at least one second carboxylic group. Estolides may be naturally occurring or synthetically derived. Exemplary synthetic estolides include, but are not limited to, oligomeric/polymeric compounds comprising two or more fatty acid residues, which may be formed by the addition of one fatty acid to the hydrocarbon backbone of a second fatty acid residue via an addition reaction across a site of unsaturation, or a condensation reaction with a hydroxyl group. Naturally occurring estolides may include esto-glyceride type compounds (e.g., triacylglycerol estolides), such as those found in certain hydroxy-containing triglycerides of the genus *lesquerella, mallotus,* or *trewia.*

"Compounds" refers to compounds encompassed by structural Formula I and II herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I and II include, but are not limited to, optical isomers of compounds of Formula I and II, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I and II cover all asymmetric variants of the compounds described herein, including isomers, racemates, enantiomers, diastereomers, and other mixtures thereof. In addition, compounds of Formula I and II include Z- and E-forms (e.g., cis- and trans-forms) of compounds with double bonds. The compounds of Formula I and II may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or sp$^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Substituted" refers to a group in which one or more hydrogen atoms are independently replaced with the same or different substituent(s). Examples of substituents include, but are not limited to, $-R^{64}$, $-R^{60}$, $-O^-$, $-OH$, $=O$, $-OR^{60}$, $-SR^{60}$, $-S^-$, $=S$, $-NR^{60}R^{61}$, $=NR^{60}$, $-CN$, $-CF_3$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$, $-C(NR^{62})NR^{60}R^{61}$, $-S(O)_2$, $NR^{60}R^{61}$, $-NR^{63}S(O)_2R^{60}$, $-NR^{63}C(O)R^{60}$, and $-S(O)R^{60}$;

wherein each $-R^{64}$ is independently a halogen; each $R^{60}$ and $R^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings;

wherein the "substituted" substituents, as defined above for $R^{60}$, $R^{61}$, $R^{62}$, and $R^{63}$, are substituted with one or more, such as one, two, or three, groups independently selected from alkyl, -alkyl-OH, —O-haloalkyl, -alkyl-NH$_2$, alkoxy, cycloalkyl, cycloalkylalkyl, heterocycloalkyl, heterocycloalkylalkyl, aryl, heteroaryl, arylalkyl, heteroarylalkyl, —O$^-$, —OH, =O, —O-alkyl, —O-aryl, —O-heteroarylalkyl, —O-cycloalkyl, —O-heterocycloalkyl, —SH, —S$^-$, =S, —S-alkyl, —S-aryl, —S— heteroarylalkyl, —S-cycloalkyl, —S-heterocycloalkyl, —NH$_2$, =NH, —CN, —CF$_3$, —OCN, —SCN, —NO, —NO$_2$, =N$_2$, —N$_3$, —S(O)$_2$O$^-$, —S(O)$_2$, —S(O)$_2$OH, —OS(O$_2$)O$^-$, —SO$_2$ (alkyl), —SO$_2$(phenyl), —SO$_2$(haloalkyl), —SO$_2$NH$_2$, —SO$_2$NH(alkyl), —SO$_2$NH(phenyl), —P(O)(O$^-$)$_2$, —P(O)(O-alkyl)(O$^-$), —OP(O)(O-alkyl)(O-alkyl), —CO$_2$H, —C(O)O(alkyl), —CON(alkyl)(alkyl), —CONH(alkyl), —CONH$_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

All numerical ranges herein include all numerical values and ranges of all numerical values within the recited range of numerical values.

Described herein are polyester compounds and compositions, including products containing estolide compounds, and methods of processing, recycling, and/or reusing the same. In certain embodiments, such compositions may include new or used lubricant products containing one or more estolide compounds.

In certain embodiments, the compositions are processed through a method that includes providing a feedstock comprising at least one polyester compound, and converting the at least one polyester compound into at least one hydrocarbon product. In certain embodiments, the at least one polyester compound comprises an estolide. In certain embodiments, converting the at least one polyester compound comprises deoxygenation. In certain embodiments, converting the at least one polyester compound comprises decarboxylation and/or decarbonylation. In certain embodiments, converting the at least one polyester compound comprises exposing said polyester to heating conditions. In certain embodiments, the process comprises contacting the at least one polyester compound with at least one catalyst, optionally in the presence of elevated heat and/or pressure. In certain embodiments, the at least one hydrocarbon product undergoes further processing to provide at least one second hydrocarbon product.

The feedstocks described herein can be any composition or formulation comprising at least one polyester compound, such as an estolide. Exemplary feedstocks include, but are not limited to, used lubricant compositions such as motor oils, marine oils, greases, hydraulic fluids, dielectric fluids, cooking oils, and the like. The processes described herein are flexible and selection of the feedstock may be based on availability and cost. In certain embodiments, the compositions are converted to a hydrocarbon product under thermal and/or catalytic conditions.

In certain embodiments, the hydrocarbon product is prepared by a process that comprises the deoxygenation of the at least one polyester. Exemplary deoxygenation processes may include decarbonylation and/or decarboxylation, wherein oxygen is removed from the at least one polyester via a reaction with hydrogen and/or the cracking of CO/CO$_2$ groups. In certain embodiments, the hydrocarbon product is obtained via the hydrotreatment of a composition comprising one or more polyesters, which is accomplished in the presence of free hydrogen gas. The preparation of the hydrocarbon product may optionally include the use of at least one catalyst. In certain embodiments, the processing of the polyester is accomplished at temperatures of greater than about 50° C. and/or a pressure of greater than 1 atm abs.

In certain embodiments, the at least one catalyst comprises a metal catalyst. In certain embodiments, the at least one catalyst comprises a transition metal, an alkali metal, or an alkaline earth metal, such as a metal selected from at least one of a Group IIA metal, a Group VIIIB metal, a Group IIB metal, a Group IIIB metal, a Group IVB metal, or a Group VIB metal. In certain embodiments, the at least one catalyst comprises a metal selected from one or more of calcium, magnesium, cobalt, iron, nickel, tungsten, chromium, molybdenum, platinum, palladium, zirconium, ytterbium, or niobium. In certain embodiments, the at least one catalyst is a monometallic catalyst, such as a metal oxide (e.g., CaO, MgO, hydrotalcite). In certain embodiments, the at least one catalyst is a multimetallic catalyst, such as a bimetallic catalyst (e.g., NiMo, CoMo, PtPd, and NiW).

In certain embodiments, the at least one catalyst may be reduced, such as by treating the catalyst with hydrogen, optionally at elevated temperatures, such as from about 100° C. to about 400° C. The catalyst temperature may be increased during hydrogen flow, such as starting at a temperature of about 130° C. and increasing to a temperature of 250° C. or 350° C. In certain embodiments, the catalyst is sulfided by contacting it with a sulfur-containing compound such as a thiol, a sulfide, a disulfide, $H_2S$, or combinations thereof, optionally at elevated temperatures. In certain embodiments, the at least one catalyst is sulfided prior to processing the at least one polyester by introducing sulfur-containing compounds, such as a thiol, a sulfide, a disulfide, $H_2S$, or combinations of thereof, in the catalyst feed. In certain embodiments, sulfiding may be desirable for the long term activity of the catalyst, depending on reaction conditions and feed compositions.

In certain embodiments, the processing of the at least one polyester may further comprise the use of a promoter, such as an element selected from Group IB or IIB of the periodic table, such as one or more of tin, copper, gold, and silver.

In certain embodiments, the at least one catalyst further comprises a support, such as a solid support. In certain embodiments, the support comprises an acid and/or oxide support. Exemplary supports include one or more oxides such as a mono- or mixed metal oxide, or a zeolite. In certain embodiments, the support comprises porous solids with high total surface areas (external and internal) which may provide high concentrations of active sites per unit weight of the at least one catalyst. In certain embodiments, the support comprises one or more oxides having a surface area greater than 20 $m^2/g$, such as greater than 75 $m^2/g$, or even 100 $m^2/g$. In certain embodiments, the surface area is less than 300 $m^2/g$.

In certain embodiments, the support comprises one or more of silica, alumina, titania, titania-alumina, titania-silica, calcium oxide, barium oxide, zirconia, lanthanum oxide, magnesium oxide, kieselguhr, silica-alumina, including zeolites, and zinc oxide. In certain embodiments, the support comprises one or more of alumina, silica, titania, zirconia, kieselguhr, and silica-alumina. In certain embodiments, the support comprises alumina, silica, and/or kieselguhr. In certain embodiments, the support comprises a zeolite.

In certain embodiments, the at least one catalyst further comprises one or more other materials, such as one or more materials selected carbon (e.g., activated charcoal, graphite, or fibril nanotube carbon), calcium carbonate, calcium silicate and barium sulfate.

In certain embodiments, the at least one catalyst is associated with the support via physically mixing the catalyst with the support material. In certain embodiments, the catalyst/support combination is prepared by co-extrusion or pelletization. For example, preparation of the at least one catalyst with a zeolite support may be completed by co-extruding or pelletizing the catalyst and zeolite after intimately mixing the two. Without being bound to any particular theory, in certain embodiments, it is believed that the composition of the hydrocarbon product can be altered depending on the identity of the catalyst/support combination, as well as the manner in which the catalyst/support combination is prepared.

In certain embodiments, the at least one catalyst and/or the support are produced by a process that includes calcination. For example, in certain embodiments, catalysts and/or supports comprising a metal oxide (i.e., CaO) are prepared via calcination.

In certain embodiments, the content range of the at least one catalyst in the catalyst/support combination comprises from about 0.1 wt % to about 90 wt % total supported catalyst. In certain embodiments, the range is from about 0.2 wt % to about 75 wt %. In certain embodiments, the range is from about 0.5 wt % to about 60 wt %.

In certain embodiments, the at least one hydrocarbon product comprises a higher ratio of odd-numbered to even-numbered hydrocarbons. In certain embodiments, a hydrocarbon product comprising a higher ratio of odd-numbered to even-numbered hydrocarbons may be achieved by a process that includes the use of a nickel catalyst. In certain embodiments, the nickel catalyst will exclude the presence of molybdenum. In certain embodiments, the catalyst/support combination comprises at least 40 wt % of nickel (combined nickel and nickel oxide). In certain embodiments, the catalyst/support combination comprises about 40 wt % to about 90 wt %, such as about 45 wt % to about 60 wt %.

In certain embodiments, the at least one hydrocarbon product comprises a higher ratio of even-numbered to odd-numbered hydrocarbons. In certain embodiments, a hydrocarbon product comprising a higher ratio of even-numbered to odd-numbered hydrocarbons may be achieved by a process that includes the use of a molybdenum catalyst. In certain embodiments, the process further comprises a cobalt catalyst. In certain embodiments, the process further comprises a nickel catalyst. In certain embodiments, nickel content of the catalyst/support comprises about 0.2 wt % to about 20 wt %, such as about 0.5 wt % to about 15 wt %.

In certain embodiments, the zeolite can be present in any amount, such as an amount of at least 10 wt %, based on the total catalyst weight, to achieve the desired hydrocracking and/or hydroisomerization. In certain embodiments, the zeolite is present in an amount of at least 25 wt %, such as 25-50 wt %.

In certain embodiments, the at least one polyester is converted into a hydrocarbon product via a process that includes cracking and/or deoxygenation. In certain embodiments, the process comprises hydrotreating, wherein free hydrogen is implemented in one or more of the processing stages. In certain embodiments, hydrotreating comprises one or more reactions selected from hydrodeoxygenation (HDO), hydroisomerization (HI) and hydrocracking (HC). In certain embodiments, HDO generally comprises the removal of oxygen as water by adding hydrogen, thereby converting the at least one polyester into the at least one hydrocarbon product. Depending on the processing conditions implemented, deoxygention of the at least one polyester may comprise one or more of decarbonylation, decarboxylation and hydrodeoxygenation. Decarboxylation may involve the process of removal of oxygen as carbon dioxide, thereby producing a paraffinic hydrocarbon. Decarbonylation may refer to the process of removal of the oxygen as carbon monoxide and water, directly creating an unsaturated hydrocarbon or indirectly by adding hydrogen to produce a saturated hydrocarbon. In decarboxylation and decarbonylation, the resulting hydrocarbon is one carbon unit shorter than the corresponding carboxylic acid residue. In hydrodeoxygenation, the resulting hydrocarbon has the same number of carbons as the corresponding carboxylic acid residue. In certain embodiments, the at least one hydrocarbon product comprises a $C_{10}$ to $C_{20}$ hydrocarbon.

In certain embodiments, the process may be tailored to control the route of oxygen removal. For processes that desire minimal use of hydrogen, the decarboxylation and direct decarbonylation routes can be used. For a process that desires minimal evolution of carbon monoxide and carbon dioxide, the indirect decarbonylation or hydrodeoxygenation are the preferred routes.

The chain length of the polyester may play a role in determining which particular deoxygenation process to use. For feeds comprising 18-carbon chains, there may be a desire for n-heptadecane (product of decarbonylation or decarboxylation) or n-octadecane (product of hydrodeoxygenation with hydrogen consumption). n-Heptadecane ($C_{17}$) has a lower melting point than n-octadecane ($C_{18}$), which in turn may affect the cold-performance characteristics of the hydrocarbon product (e.g., a diesel blending stock). Additionally, producing $C_{17}$ removes oxygen from the polyester primarily as CO and/or $CO_2$ (reduced hydrogen consumption) whereas making $C_{18}$ hydrocarbons removes oxygen primarily in the form of $H_2O$ (reduced greenhouse gas emissions). Depending on the conditions, either $C_{17}$ or $C_{18}$ hydrocarbons may be desirable. These routes may be selectively controlled by varying the type and/or composition of the catalyst as described herein.

In certain embodiments, the hydrocarbon product will comprise a similar molecular structure to the hydrocarbon backbone of the original polyester feed. For example, the processing of a polyester (e.g., an estolide) comprised primarily of linear $C_{18}$ carboxylic acid residues (e.g., stearic acid and oleic acid) will result in a hydrocarbon product comprised primarily of linear $C_{17}$ and/or $C_{18}$ chain lengths. In certain embodiments, linear hydrocarbons may provide good cetane numbers, but may also possess poor cold weather capabilities. In other circumstances, it may simply be desirable to pursue hydrocarbon products having shorter chain lengths, branching, and/or varying levels of saturation. Accordingly, in certain embodiments, the hydrocarbon product is exposed to further processing to provide at least one second hydrocarbon product. In certain embodiments, the at least one second hydrocarbon product comprises a $C_4$ to $C_{10}$ hydrocarbon that is branched or unbranched.

In certain embodiments, the hydrocarbon product and/or second hydrocarbon product may be prepared by any of the processing steps previously described herein. In certain embodiments, the polyester and/or hydrocarbon product may be exposed to isomerization and/or cracking, which may improve the cold weather properties (e.g., lowers pour point). In certain embodiments, the isomerization comprises hydroisomerization. In certain embodiments, the cracking comprises hydrocracking. In certain embodiments, the isomerization converts a linear hydrocarbon into a branched hydrocarbon. In certain embodiments, a hydrocarbon product comprising a branched hydrocarbon may boil in the range of petro diesel.

The "cracking" of a compound may generally refer to the reduction in size of a molecule. For example, a compound comprising fatty acid residues may be cracked during decarboxylation, wherein $CO_2$ is removed from the resulting hydrocarbon chain. In certain embodiments, cracking of the hydrocarbon chain itself results in the shortening of the hydrocarbon chain, wherein carbon-carbon bonds are broken. In certain embodiments, the cracking comprises thermal decarboxylation, wherein decarboxylation takes place under heating conditions, with or without the presence of a catalyst. In certain embodiments, the cracking comprises HC, wherein free hydrogen is present. In certain embodiments, HC will further result in the desulfurization and/or denitrification of the feedstock. Hydrocarbons having a reduced chain length may provide a lower melting component in green diesel or as an additive to petro diesel.

In certain embodiments, converting the at least one polyester comprises the presence of water. For example, in certain embodiments, it may be desirable to first hydrolytically cleave the polyester (e.g., estolide) under thermal and/or catalytic conditions, thereby providing free fatty acid intermediates. Further exposure to heat and/or catalytic conditions will result in the deoxygenation and/or cracking of the free fatty acid intermediates to provide the at least one hydrocarbon product.

In certain embodiments, it may be desirable to combine one or more of the processes described herein to the preparation of the at least one hydrocarbon product. In certain embodiments, converting the polyester into at least one hydrocarbon product, and exposing the at least one hydrocarbon product to further processing, may be accomplished by using the same catalyst.

As noted above, in certain embodiments the feedstock may further comprise one or more additional components, including petroleum-based oils such as Group I-III base oils and polyalphaolefins. Accordingly, in certain embodiments, it may be desirable to also process one or more of the additional components of the feedstock. In certain embodiments, the processing of the additional component(s) may occur during the converting of the polyester into at least one hydrocarbon product. Alternatively, or in addition, the additional component(s) may be processed during a further processing step of the at least one hydrocarbon product. In certain embodiments, the additional component(s) may be substantially separated from the feedstock prior to converting the at least one polyester, such that any processing of the additional component(s) occurs separately from the converting of the at least one polyester and/or the further processing of the at least one hydrocarbon product. In certain embodiments, processing the one or more additional components comprises cracking, isomerization, hydrogenation, desulfurization, and/or denitrification.

In certain embodiments, implementation of the processes described herein comprises exposing the feedstock, the at least one polyester, the at least one hydrocarbon product, and/or the additional component(s) to elevated temperatures and/or pressures. In certain embodiments, the processes further comprise contacting the feedstock, the at least one polyester, the at least one hydrocarbon product, and/or the additional component(s) with a catalyst, such as one or more of the catalysts described herein, and/or free hydrogen. In certain embodiments, the elevated temperature is at least 50° C., at least 100° C., at least 150° C., at least 200° C., at least 250° C., at least 300° C., at least 350° C., at least 400° C., at least 450° C., at least 500° C., at least 550° C., or at least 600° C. In certain embodiments, the elevated temperature is about 250° C. to about 1000° C., about 200° C. to about 500° C., about 300° C. to about 700° C., about 350° C. to about 600° C., about 250° C. to about 1000° C., or about 400° C. to about 550° C. In certain embodiments, the elevated pressure is greater than 1 atmosphere absolute (atm abs). In certain embodiments, the elevated pressure is greater than 5 atm abs, 10 atm abs, 50 atm abs, 100 atm abs, or 150 atm abs. In certain embodiments, the elevated pressure is about 10 atm abs to about 200 atm abs, or about 20 atm abs to about 150 atm abs.

In certain embodiments, the process comprises providing a feedstock comprising at least one polyester compound, and converting the at least one polyester compound into at least one hydrocarbon product. In certain embodiments, the process comprises the hydrodeoxygenation of a feedstock comprising at least one polyester compound. In certain embodiments, the converting comprises contacting the at least one polyester with a catalyst in the presence of hydrogen. In certain embodiments, the converting is conducted at a temperature of about 200° C. to about 500° C. and a pressure of 10 atm abs to 200 atm abs. In certain embodiments, the catalyst comprises at least one metal selected from nickel, cobalt, molybdenum, or tungsten. In certain embodiments, the process further comprises the use of at least one metal oxide, such as a metal oxide previously described herein. In certain embodiments, the at least one catalyst is in a reduced form. In certain embodiments, the process produces a hydrocarbon product having a ratio of odd-numbered hydrocarbons to even-numbered hydrocarbons of at least 2:1, at least 3:1, at least 5:1, or at least 10:1. When the feedstock comprises over 50% $C_{18}$-based components, such as certain estolides, the process generally favors decarbonylation and/or decarboxylation rather than hydrodeoxygenation.

In certain embodiments, under similar temperature and/or pressure conditions described in the foregoing, the catalyst comprises molybdenum and at least one of nickel or cobalt. In certain embodiments, the catalyst is optionally sulfided prior to use. Consequently, in certain embodiments when the feedstock comprises over 50% $C_{18}$-based components, such as certain estolides, the process generally favors hydrodeoxygenation rather than decarbonylation and/or decarboxylation.

The processes described herein may be conducted in any suitable type of reactor. Exemplary reactors include, but are not limited to, fixed bed reactors and slurry reactors. In certain embodiments, a fixed bed reactor has an advantage of easy separation of the reactants and products from the catalyst. Fixed bed reactors may include plug flow and trickle bed reactors. Fixed bed reactors may be of the type adiabatic, multi-tubular, continuous recirculating packed bed reactor. Exemplary slurry reactors may include batch, a continuously stirred tank reactor, and a bubble column reactor. In the slurry reactors, the catalyst may be removed from the reaction mixture by filtration or centrifugal action. In certain embodiments, the processes described herein comprise a continuous process, and the reactor comprises a fixed bed or continuously stirred tank reactor. In certain embodiments, the process comprises a continuous process and the reactor comprises a fixed bed reactor.

In certain embodiments, the process is a continuous process in a fixed bed or slurry reactor and the catalyst is in the form of particles, such as shaped particles. As used herein, a shaped particle comprises the form of an extrudate. Exemplary extrudates may include cylinders, pellets, or spheres. Cylinder shapes may have hollow interiors with one or more reinforcing ribs. Trilobe, cloverleaf, rectangular- and triangular-shaped tubes, cross, and "C"-shaped catalysts may also be used.

In certain embodiments, the shaped catalyst particle is about 0.01 to about 0.5 inch (about 0.25 to about 13 mm) in diameter when a packed bed reactor is used. In certain embodiments, the catalyst particle is about 1/32 to about 1/4 inch (about 0.79 to about 6.4 mm) in diameter.

A wide range of suitable catalyst concentrations may be used. The amount of catalyst per reactor may depend on the reactor type. In certain embodiments, for a fixed bed reactor, the volume of catalyst per reactor may be high, while in a slurry, the volume may be lower. In certain embodiments, in a slurry reactor, the catalyst will make up 0.1 to about 30 wt % of the reactor contents. In certain embodiments, the catalyst is 1 to 15 wt % of the reactor contents.

In certain embodiments, for a fixed bed reactor, the weight hourly space velocity may typically fall in the range of 0.05 to 100 $hr^{-1}$, such as 0.1 to 10 $hr^{-1}$ or 1.0 to 5.0 $hr^{-1}$.

In certain embodiments, the feedstock comprising the polyester is contacted with hydrogen to form a liquid feed/hydrogen mixture in advance of contacting the liquid feed/hydrogen mixture with the catalyst. Optionally, a solvent or diluent, having a relatively high solubility for hydrogen so that substantially all the hydrogen is in solution, can be added to the feed and hydrogen in advance of contacting with the catalyst to form a liquid feed/solvent or liquid feed/diluent mixture. The liquid feed/solvent or liquid feed/diluent mixture is then contacted with hydrogen to form a liquid feed/solvent/hydrogen or liquid feed/diluent/hydrogen mixture. The mixture containing hydrogen is then contacted with the catalyst.

In certain embodiments, the liquid feed/solvent/hydrogen or liquid feed/diluent/hydrogen mixture is contacted with catalyst in a packed bed reactor, such as plug flow, tubular or other fixed bed reactor for feed and hydrogen to react. In certain embodiments, the packed bed reactor may be a single packed bed or multiple beds in series or in parallel or in a combination thereof as discussed hereinabove.

In certain embodiments, the liquid feed/solvent/hydrogen or liquid feed/diluent/hydrogen mixture can be a substantially hydrogen-gas-free liquid feed stream. The feed stream may be produced by contacting liquid feed with hydrogen and solvent or diluent to produce a hydrogen-saturated liquid feed. Alternatively or in addition, after contacting liquid feed with hydrogen and solvent or diluent, hydrogen gas may be removed from the feed stream, for example, by known gas/liquid separation methods in a disengagement step.

In certain embodiments, the percentage of hydrogen soluble in the solvent/diluent is greater than the percentage of hydrogen soluble in the liquid feed reactant. Thus, in certain embodiments, all of the hydrogen required for reaction is made available in solution upstream of the fixed bed reactor, thus eliminating the need to circulate hydrogen gas within the reactor.

In certain embodiments, the reaction of liquid feed/solvent/hydrogen or liquid feed/diluent/hydrogen mixture with catalyst is highly exothermic and as a result a great deal of heat is generated in the reactor. In certain embodiments, the temperature of the reactor can be controlled by using a recycle stream. In certain embodiments, at least a portion of the hydrocarbon product can be recycled back to the front of the reactor as a recycle stream and blended with fresh feed and hydrogen for use as solvent or diluent.

In certain embodiments, the process comprises a multistage process using a series of two or more reactors in series and fresh hydrogen can be added at the inlet of each reactor. In certain embodiments, the recycle stream absorbs some of the heat and reduces the temperature rise through the reactor. In certain embodiments, the reactor temperature can be controlled by controlling the fresh feed temperature and the amount of recycle. In addition, because the recycle stream comprises reacted components, the recycle stream may also serve as an inert diluent.

In certain embodiments, the type and amount of diluent added, as well as the reactor conditions, can be set so that substantially all of the hydrogen required in the hydrotreating reactions is available in solution. The solvent or diluent may comprise a portion of the reactor effluent used as a recycle stream, but can alternatively be selected from light hydrocarbons, light distillates, naphtha, diesel, or the like. Examples include propane, butanes, and/or pentanes. The percentage of hydrogen in the solvent or diluent may be greater than the percentage of hydrogen in the feed, thus, in this embodiment, all of the hydrogen required for reaction is made available in solution upstream of the reactor and eliminating the need to re-circulate hydrogen gas co-eluting with the effluent or product stream.

In certain embodiments, the processes described herein may be used to produce green diesel. Green diesel produced in the process may have the desired properties for use as diesel or for blending with petro diesel. In certain embodiments, a linear product having a high cetane number is produced, which may be necessary to maintain power for diesel engines to run efficiently. In certain embodiments, the product can be used as fuel alone, or blended into lower cetane products, such as light cycle oil, oil sands or kerosene.

In certain embodiments, a green diesel produced from one or more of the processes described herein raises the cetane number without negatively impacting the density. In certain embodiments, cetane numbers can be controlled by the selection of the specific catalyst and the process conditions. In certain embodiments, cetane numbers may be desired in the range of 50 to 100, such as 70 to 100. In certain embodiments, the branching of some of the chains and the cracking into smaller chains lowers the cloud point temperatures that would allow its usage in cold weather applications down to −40° C., such as when blended in cold climate petro diesel. In certain embodiments, the degree of branching is dependent on the temperature of the application and can be controlled by the selection of certain zeolites that may be used in the process, as well as the type and the combination of the catalyst. In certain embodiments, green diesel produced by this process may also exhibit the desired lubricity (400 to 650 microns), viscosity (3 to 5 cSt at 40° C.), and density (750 to 800 kg/m³ at 25° C.), which may be suitable for today's diesel engines.

In certain embodiments, the processes described herein provide for more economical production and implementation of green diesel with little or no impact on current refining production facilities or current diesel engines.

In certain embodiments, the feedstock comprises at least one polyester compound. In certain embodiments, the feedstock comprises a composition selected from motor oils, marine oils, greases, hydraulic fluids, dielectric fluids, cooking oils, and the like. Accordingly, in certain embodiments, the feedstock may comprise one or more additional components, such as additives (e.g., antioxidants and antiwear agents), synthetic base oils (e.g., polyalphaolefins; polyakylene glycols), esters (e.g., triglycerides), and petroleum base stocks (e.g., Group I, II, or III base oils). Thus, in certain embodiments, processing of the feedstock will provide a hydrocarbon product, wherein at least a portion of the hydrocarbon product is derived from the one or more additional components. In certain embodiments, the at least one polyester comprises at least one estolide compound. In certain embodiments, the at least one estolide compound is selected from compounds of Formula I:

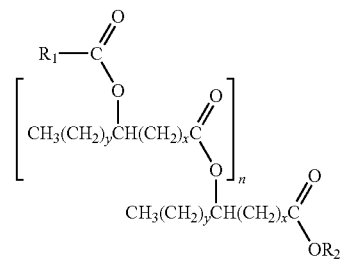

Formula I wherein $x$ is, independently for each occurrence, an integer selected from 0, 1, 2, 3, 4, 5, 6, 7, 8, 9, 10, 11, 12, 13, 14, 15, 16, 17, 18, 19, and 20;

$y$ is, independently for each occurrence, an integer selected from 0, 1, 2, 3, 4, 5, 6, 7, 8, 9, 10, 11, 12, 13, 14, 15, 16, 17, 18, 19, and 20;

$n$ is equal to or greater than 0;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

In certain embodiments, the at least one estolide compound is selected from compounds of Formula II:

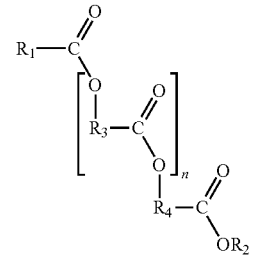

Formula II wherein $n$ is an integer equal to or greater than 0;

$R_1$ is an optionally substituted alkyl that is saturated or unsaturated, and branched or unbranched; and $R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In certain embodiments, the composition comprises at least one estolide of Formula I or II where $R_1$ is hydrogen.

The terms "chain" or "fatty acid chain" or "fatty acid chain residue," as used with respect to the estolide compounds of Formula I and II, refer to one or more of the fatty acid residues incorporated in estolide compounds, e.g., $R_3$ or $R_4$ of Formula II, or the structures represented by $CH_3(CH_2)_y CH(CH_2)_x C(O)O$— in Formula I.

The $R_1$ in Formula I and II at the top of each Formula shown is an example of what may be referred to as a "cap" or "capping material," as it "caps" the top of the estolide. Similarly, the capping group may be an organic acid residue of general formula —OC(O)-alkyl, i.e., a carboxylic acid with a substituted or unsubstituted, saturated or unsaturated, and/or branched or unbranched alkyl as defined herein, or a formic acid residue. In certain embodiments, the "cap" or "capping group" is a fatty acid. In certain embodiments, the capping group, regardless of size, is substituted or unsubstituted, saturated or unsaturated, and/or branched or unbranched. The cap or capping material may also be referred to as the primary or alpha (α) chain. The $R_4C(O)O-$ of Formula II or structure $CH_3(CH_2)_yCH(CH_2)_xC(O)O-$ of Formula I serve as the "base" or "base chain residue" of the estolide. The base or base chain residue may also be referred to as tertiary or gamma (γ) chains.

The $R_3C(O)O-$ of Formula II or structure $CH_3(CH_2)_yCH(CH_2)_xC(O)O-$ of Formula I are linking residues that link the capping material and the base fatty-acid residue together. There may be any number of linking residues in the estolide, including when n=0 and the estolide is in its dimer form. Depending on the manner in which the estolide is prepared, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic group of another fatty acid. In some embodiments, it may be desirable to have a linking fatty acid that is monounsaturated so that when the fatty acids link together, all of the sites of unsaturation are eliminated. The linking residue(s) may also be referred to as secondary or beta (β) chains.

In certain embodiments, the cap is an acetyl group, the linking residue(s) is one or more fatty acid residues, and the base chain residue is a fatty acid residue. In certain embodiments, the linking residues present in an estolide differ from one another. In certain embodiments, one or more of the linking residues differs from the base chain residue.

Estolides may be prepared according to any method known to those of skill in the art. As noted above, in certain embodiments, unsaturated fatty acids such as mono- and/or polyunsaturated fatty acids may be used. For example, monounsaturated fatty acids, along with a suitable catalyst, will form a single carbocation that allows for the addition of a second fatty acid, whereby a single link between two fatty acids is formed. Suitable monounsaturated fatty acids may include, but are not limited to, palmitoleic acid (16:1), vaccenic acid (18:1), oleic acid (18:1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5). Other exemplay fatty acids may include terminally-unsaturated fatty acids such as 10-undecenoic acid, which may be derived from castor oil. In certain embodiments, hydroxy fatty acids may be polymerized or homopolymerized by reacting the carboxylic acid functionality of one fatty acid with the hydroxy functionality of a second fatty acid. Exemplary hydroxyl fatty acids include, but are not limited to, ricinoleic acid, 6-hydroxystearic acid, 9,10-dihydroxystearic acid, 12-hydroxystearic acid, and 14-hydroxystearic acid.

The process for preparing the estolide compounds described herein may include the use of any natural or synthetic carboxylic acid source. However, it may be desirable to source the carboxylic acids from a renewable biological feedstock. Suitable starting materials of biological origin may include plant fats, plant oils, plant waxes, animal fats, animal oils, animal waxes, fish fats, fish oils, fish waxes, algal oils and mixtures thereof. Other potential carboxylic acid sources may include waste and recycled food-grade fats and oils, fats, oils, and waxes obtained by genetic engineering, fossil fuel-based materials and other sources of the materials desired.

In certain embodiments, the estolide compounds described herein may be prepared from non-naturally occurring fatty acids derived from naturally occurring feedstocks. In certain embodiments, the estolides are prepared from synthetic fatty acid reactants derived from naturally occurring feedstocks such as vegetable oils. For example, the synthetic fatty acid reactants may be prepared by cleaving fragments from larger fatty acid residues occurring in natural oils such as triglycerides using, for example, a cross-metathesis catalyst and alpha-olefin(s). The resulting truncated fatty acid residue(s) may be liberated from the glycerine backbone using any suitable hydrolytic and/or transesterification processes known to those of skill in the art. An exemplary fatty acid reactants include 9-dodecenoic acid and 9-decenoic acid, which may be prepared via the cross metathesis of an oleic acid residue with 1-butene.

In some embodiments, the estolide comprises fatty-acid chains of varying lengths. In some embodiments, x is, independently for each occurrence, an integer selected from 0 to 20, 0 to 18, 0 to 16, 0 to 14, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20. In certain embodiments, for at least one fatty acid chain residue, x is an integer selected from 7 and 8.

In some embodiments, y is, independently for each occurrence, an integer selected from 0 to 20, 0 to 18, 0 to 16, 0 to 14, 1 to 12, 1 to 10, 2 to 8, 6 to 8, or 4 to 6. In some embodiments, y is, independently for each occurrence, an integer selected from 7 and 8. In some embodiments, y is, independently for each occurrence, an integer selected from 0, 1, 2, 3, 4, 5, 6, 7, 8, 9, 10, 11, 12, 13, 14, 15, 16, 17, 18, 19, and 20. In some embodiments, for at least one fatty acid chain residue, y is an integer selected from 0 to 6, or 1 and 2. In certain embodiments, y is, independently for each occurrence, an integer selected from 1 to 6, or 1 and 2. In certain embodiments, y is 0.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y is 15 for each chain. In some embodiments, x+y is, independently for each chain, an integer selected from 6, 7, 8, 9, 10, 11, 12, 13, 14, 15, 16, 17, 18, 19, 20, 21, 22, 23, and 24. In certain embodiments, for at least one fatty acid chain residue, x+y is an integer selected from 9 to 13. In certain embodiments, for at least one fatty acid chain residue, x+y is 9. In certain embodiments, x+y is, independently for each chain, an integer selected from 9 to 13. In certain embodiments, x+y is 9 for each fatty acid chain residue. In certain embodiments, x is 7 and y is 0, wherein x+y is 7.

In some embodiments, the estolide compound of Formula I or II may comprise any number of fatty acid residues to form an "n-mer" estolide. For example, the estolide may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is 1, wherein said at least one compound of Formula I or II comprises the trimer. In some embodiments, n is greater than 1. In some embodiments, n is an integer selected from 0, 1, 2, 3, 4, 5, 6, 7, 8, 9, 10, 11, 12, 13, 14, 15, 16, 17, 18, 19, and 20.

In certain embodiments, the estolide compounds and compositions described herein exhibit high- and ultra-high viscosities. In certain embodiments, such high- and ultra-high viscosity properties may be attributable to the size of the estolide oligomer, i.e., the estolide number (EN) of the estolide and the value of "n" with regard to Formula I and II. Thus, in certain embodiments, n is an integer selected from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. In certain embodiments, n is an integer selected from 10 to 30, 15 to 30, 20 to 30, or 15 to 25.

In some embodiments, $R_1$ of Formula I or II is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_1$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_1$ is selected from $C_{13}$ to $C_{17}$ alkyl, such as from $C_{13}$ alkyl, $C_{15}$ alkyl, and $C_{17}$ alkyl. In some embodiments, $R_1$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_2$ of Formula I or II is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_2$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_2$ is selected from $C_{13}$ to $C_{17}$ alkyl, such as from $C_{13}$ alkyl, $C_{15}$ alkyl, and $C_{17}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_3$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_3$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_3$ is selected from $C_{13}$ to $C_{17}$ alkyl, such as from $C_{13}$ alkyl, $C_{15}$ alkyl, and $C_{17}$ alkyl. In some embodiments, $R_3$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_4$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_4$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_4$ is selected from $C_{13}$ to $C_{17}$ alkyl, such as from $C_{13}$ alkyl, $C_{15}$ alkyl, and $C_{17}$ alkyl. In some embodiments, $R_4$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, the estolide is in its free-acid form, wherein $R_2$ of Formula I or II is hydrogen. In some embodiments, $R_2$ is selected from optionally substituted alkyl that is saturated or unsaturated, and branched or unbranched. In certain embodiments, the $R_2$ residue may comprise any desired alkyl group, such as those derived from esterification of the estolide with the alcohols identified in the examples herein. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ may be selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, in certain embodiments, $R_2$ may be branched, such as isopropyl, isobutyl, or 2-ethylhexyl. In some embodiments, $R_2$ may be a larger alkyl group, branched or unbranched, comprising $C_{12}$ alkyl, $C_{16}$ alkyl, $C_{18}$ alkyl, or $C_{20}$ alkyl.

In some embodiments, the compounds described herein may comprise a mixture of two or more estolide compounds of Formula I and II. It is possible to characterize the chemical makeup of an estolide, a mixture of estolides, or a composition comprising estolides, by using the compound's, mixture's, or composition's measured estolide number (EN) of compound or composition. The EN represents the average number of fatty acids added to the base fatty acid. The EN also represents the average number of estolide linkages per molecule:

$$EN = n+1$$

wherein n is the number of secondary (β) fatty acids. Accordingly, a single estolide compound will have an EN that is a whole number, for example for dimers, trimers, and tetramers:

dimer EN=1
trimer EN=2
tetramer EN=3

However, a composition comprising two or more estolide compounds may have an EN that is a whole number or a fraction of a whole number. For example, a composition having a 1:1 molar ratio of dimer and trimer would have an EN of 1.5, while a composition having a 1:1 molar ratio of tetramer and trimer would have an EN of 2.5.

In some embodiments, the compositions may comprise a mixture of two or more estolides having an EN that is an integer or fraction of an integer that is greater than 4.5, or even 5.0. In some embodiments, the EN may be an integer or fraction of an integer selected from about 1.0 to about 5.0. In some embodiments, the EN is an integer or fraction of an integer selected from 1.2 to about 4.5. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6 and 5.8. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0, 5.2, 5.4, 5.6, 5.8, and 6.0. In some embodiments, the EN is selected from 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0. In certain embodiments, the EN is at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In certain embodiments, the EN is about 10 to about 30. In certain embodiments, the EN is about 15 to about 30. In certain embodiments, the EN is about 20 to about 40. In certain embodiments, the EN is about 20 to about 30. In certain embodiments, the EN is about 15 to about 25.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. For example, in some embodiments the estolides described herein may comprise at least one compound of Formula II:

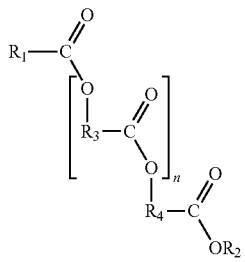

Formula II wherein n is an integer equal to or greater than 0;

$R_1$ is an optionally substituted alkyl that is saturated or unsaturated, and branched or unbranched $R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched.

In some embodiments, n is an integer selected from 1 to 20. In some embodiments, n is an integer selected from 1 to 12. In some embodiments, n is an integer selected from 1, 2, 3, 4, 5, 6, 7, 8, 9, 10, 11, 12, 13, 14, 15, 16, 17, 18, 19 and 20. In certain embodiments, n is an integer selected from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. In certain embodiments, n is an integer selected from 10 to 30, 15 to 30, 20 to 30, or 15 to 25. In some embodiments, one or more $R_3$ differs from one or more other $R_3$ in a compound of Formula II. In some embodiments, one or more $R_3$ differs from $R_4$ in a compound of Formula II. In some embodiments, if the compounds of Formula II are prepared from one or more polyunsaturated fatty acids, it is possible that one or more of $R_3$ and $R_4$ will have one or more sites of unsaturation. In some embodiments, if the compounds of Formula II are prepared from one or more branched fatty acids, it is possible that one or more of $R_3$ and $R_4$ will be branched.

In some embodiments, $R_3$ and $R_4$ can be $CH_3(CH_2)_yCH(CH_2)_x$—, where x is, independently for each occurrence, an integer selected from 0, 1, 2, 3, 4, 5, 6, 7, 8, 9, 10, 11, 12, 13, 14, 15, 16, 17, 18, 19, and 20, and y is, independently for each occurrence, an integer selected from 0, 1, 2, 3, 4, 5, 6, 7, 8, 9, 10, 11, 12, 13, 14, 15, 16, 17, 18, 19, and 20. Where both $R_3$ and $R_4$ are $CH_3(CH_2)_yCH(CH_2)_x$—, the compounds may be compounds according to Formula I.

Methods for obtaining polyesters, estolides, feedstocks, and other compostions described herein will be apparent to those of ordinary skill in the art, with exemplary procedures being described below.

EXAMPLES

Example 1

A 100 cc isothermal tubular reactor is filled with 80 cc of a commercially available NiMo catalyst (Catalyst Trading Corporation, Houston, Tex.) and 70-100 mesh glass beads. The catalyst is sulfided in the presence of hydrogen with dimethyl disulfide at two hold temperatures: 6 hrs at 200° C. and 12 hrs at 350° C. Hydrogen sulfide break-through is confirmed before the temperature is raised from 200° C. to 350° C. at 10° C./hr. After sulfiding, the reactor is cooled to 200° C. Next an estolide feed (comprising at least one estolide compound of Formula II) is introduced to the isothermal reactor. The reactor is slowly heated to 350° C. to achieve full conversion of the estolide feed to predominantly n-paraffins. The reactor temperature is further increased to 375° C. to maintain good catalyst activity at 80 cc/hr feed rate (1.0 $hr^{-1}$ LHSV). A gas chromatogram may be used to confirm the identity of hydrocarbon product, which may predominantly comprise $C_{15}$-$C_{18}$ n-paraffins (hydrocarbons) with no detectable oxygenates remaining.

Example 2

An estolide feed (comprising at least one estolide compound of Formula II) (100 g) and a reduced Ni/NiO/MgO/SiO$_2$/graphite catalyst (Pricat Ni 55/5 P, 5 g, available from Johnson Matthey, West Deptford, N.J.) are placed in a 400 cc agitated pressure reactor. The autoclave headspace is purged first with nitrogen 10 times by pressurizing/depressurizing between 7 and 1 atm abs, then with industrial grade hydrogen (high pressure 99% purity, available from GTS Inc., Morrisville, Pa., USA) 5 times, and finally pressurized to 35 atm abs with hydrogen. The autoclave and its contents are heated to 250° C. with agitation. The hydrogen pressure is increased to 140 atm abs, and maintained there for 5 hrs. The headspace is filled with fresh hydrogen to 140 atm abs if the pressure drops below 100 atm abs. The temperature is maintained 250° C. (+/−10° C.).

The autoclave contents are then cooled to below 50° C., the headspace is vented, and the contents are discharged. The contents will comprise the hydrocarbon product.

Example 3

An estolide feed (comprising at least one estolide compound of Formula II) (50 g) and the catalyst used in Example 2 are placed in a 400 cc agitated pressure reactor. The reaction is run at 300° C. and the catalyst contains USY zeolite powder (0.125 g, type EZ-190, available from Engelhard (now part of BASF), Si/Al=3.05) is physically mixed in. The reaction contents are weighed (51 g). IR will show the sample to contain hydrocarbons, with possible trace of unreacted (or partially reacted) estolide. A proton NMR analysis should demonstrate a linear paraffin (hydrocarbon) product distribution of $C_{14}$ to $C_{18}$, with $C_{17}$ being the predominant product. Some branching (isoheptadecane) may be observed.

Example 4

The process of Example 3 is repeated using the same equipment, pressure and temperature conditions, and the reactants except for the catalyst and no zeolite are added. The catalyst used is reduced nickel powder catalyst on zirconia and kieselguhr (E-473P, 2.5 g, available from BASF Catalysts, Houston, Tex., USA). The reaction products are weighed (51 g). An IR should show no remaining estolide in the sample. A GC-FID analysis should demonstrate a linear paraffin (hydrocarbon) product distribution of $C_{14}$ to $C_{18}$, with $C_{17}$ being the predominant product. Branching may not be observed.

Example 5

Example 3 is repeated using the same equipment, pressure and temperature conditions. The reactants are the same as in Example 3, but different amounts are used (100 g estolide, 5 g Ni 55/5 P catalyst, and 0.5 g of USY zeolite powder, type EZ-190). A GC-FID analysis should demonstrate a linear paraffin (hydrocarbon) product distribution of $C_{14}$ to $C_{18}$, with $C_{18}$ being the predominant product. Some isomerized product may be observed.

Example 6

An estolide feed (comprising at least one estolide compound of Formula II) is added to a batch reactor in the presence of water. The reactor is heated to 150° C. to 300° C., and hydrolysis of the estolide compounds is monitored to completion by GC-FID. In the second stage, the resulting hydroxy fatty acid intermediates are heated to 400° C. to 600° C. to effect thermal decarboxylation of the fatty acids and provide a hydrocarbon product. Water, carbon dioxide, and/or hydrogen byproducts may be collected for reuse or further processing steps.

Example 7

The processing procedures of Examples 1 through 6 are repeated, except the estolide feed is replaced with a finished lubricant formulation comprising an estolide base oil, a petroleum-based oil, and additional components [35% estolide base oil (EN=1.31; viscosity @ 40° C. ASTM D445=35.3); Group III base oil=48.15% (Yubase 4=22.95%; Yubase 6=25.20%); styrene-diene polymer=3.5% (SV277); detergent=12.2% (P5710); aminic antiox.=1.15%]. The processes provided hydrocarbon products comprising hydrocarbon components derived from both the estolide feed and the petroleum-based oil.

The invention claimed is:

1. A method comprising:
providing a feedstock comprising at least one estolide compound; and converting the at least one estolide compound into at least one hydrocarbon product, wherein the at least one estolide compound is selected from compounds of the following formula:

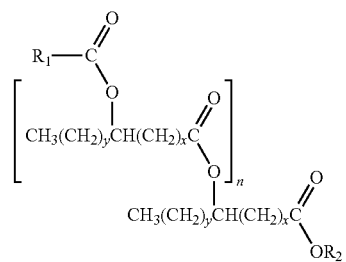

wherein
x is, independently for each occurrence, an integer selected from 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is an integer selected from 0 to 20;
$R_1$ is an optionally substituted alkyl that is saturated or unsaturated, and branched or unbranched; and
$R_2$ is selected from hydrogen and an optionally substituted alkyl that is saturated or unsaturated, and branched or unbranched;
wherein each fatty acid chain residue of said at least one estolide compound is independently optionally substituted.

2. The method according to claim 1, wherein converting the at least one estolide compound comprises deoxygenating the at least one estolide compound.

3. The method according to claim 2, wherein the deoxygenating comprises decarboxylation.

4. The method according to claim 2, wherein the deoxygenating comprises thermal decarboxylation.

5. The method according to claim 2, wherein the deoxygenating comprises decarbonylation.

6. The method according to claim 2, wherein the deoxygenating comprises hydrodeoxygenation.

7. The method according to claim 2, wherein converting the at least one estolide compound is conducted in the presence of water.

8. The method according to claim 2, wherein converting the at least one estolide compound is conducted in the presence of hydrogen.

9. The method according to claim 2, wherein converting the at least one estolide compound comprises contacting said at least one estolide compound with at least one catalyst.

10. The method according to claim 9, wherein the at least one catalyst comprises a transition metal.

11. The method according claim 2, wherein converting the at least one estolide compound is conducted at a temperature of at least 100° C.

12. The method according to claim 11, wherein converting the at least one estolide compound is conducted at a temperature of about 200° C. to about 500° C.

13. The method according to claim 2, wherein converting the at least one estolide compound is conducted at a pressure greater than 1 atm absolute.

14. The method according to claim 2, wherein the at least one hydrocarbon product comprises a $C_{10}$ to $C_{20}$ hydrocarbon.

15. The method according to claim 14, wherein the at least one hydrocarbon product comprises a $C_{17}$ hydrocarbon and/or a $C_{18}$ hydrocarbon.

16. The method according to claim 1, wherein the at least one hydrocarbon product undergoes further processing to provide at least one second hydrocarbon product.

17. The method according to claim 16, wherein the further processing comprises cracking, hydrogenation and/or isomerization.

18. The method according to claim 17, wherein the at least one second hydrocarbon product comprises a branched or unbranched $C_4$ to $C_{10}$ hydrocarbon.

19. The method according to claim 1, wherein the feedstock further comprises at least one additional component.

20. The method according to claim 19, wherein the at least one additional component comprises one or more of a Group I base oil, a Group II base oil, a Group III base oil, and a polyalphaolefin.

* * * * *